(12) United States Patent
Trehan et al.

(10) Patent No.: US 12,220,447 B2
(45) Date of Patent: Feb. 11, 2025

(54) PROTEOLYTIC ENZYME COMPOSITION

(71) Applicant: BRIGHT LIFECARE PVT. LTD, Gurgaon (IN)

(72) Inventors: Anupam Trehan, Gurgaon (IN); Manoj Kumar Verma, Gurgaon (IN); Harinder Singh, Gurgaon (IN); Tanyya Khanna, Gurgaon (IN); Puja Kumari, Gurgaon (IN); Sameer Maheshwari, Gurgaon (IN)

(73) Assignee: Bright Lifecare PVT LTD., Gurgaon (IN)

( * ) Notice: Subject to any disclaimer, the term of this patent is extended or adjusted under 35 U.S.C. 154(b) by 649 days.

(21) Appl. No.: 17/425,582

(22) PCT Filed: Nov. 26, 2019

(86) PCT No.: PCT/IN2019/050865
§ 371 (c)(1),
(2) Date: Jul. 23, 2021

(87) PCT Pub. No.: WO2020/161730
PCT Pub. Date: Aug. 13, 2020

(65) Prior Publication Data
US 2022/0088151 A1    Mar. 24, 2022

(30) Foreign Application Priority Data

Feb. 7, 2019 (IN) .............................. 201911004951
Oct. 25, 2019 (IN) .............................. 201911004951

(51) Int. Cl.
| | | |
|---|---|---|
| *A61K 38/46* | (2006.01) | |
| *A23L 29/00* | (2016.01) | |
| *A23L 33/195* | (2016.01) | |
| *A61K 38/47* | (2006.01) | |
| *A61K 38/48* | (2006.01) | |
| *C12N 9/50* | (2006.01) | |
| *C12N 9/54* | (2006.01) | |
| *C12N 9/58* | (2006.01) | |

(52) U.S. Cl.
CPC ............ *A61K 38/465* (2013.01); *A23L 29/06* (2016.08); *A23L 33/195* (2016.08); *A61K 38/47* (2013.01); *A61K 38/4826* (2013.01); *A61K 38/488* (2013.01); *C12N 9/54* (2013.01); *C12N 9/58* (2013.01); *C12N 9/63* (2013.01); *C12Y 304/22002* (2013.01); *C12Y 304/22004* (2013.01)

(58) Field of Classification Search
CPC ..... A23L 29/06; A23L 33/195; A61K 38/465; A61K 38/47; A61K 38/48; A61K 38/4826; A61K 38/4873; A61K 38/4888; C12N 9/54; C12N 9/58; C12N 9/63; C12Y 304/22002; C12Y 304/22004
See application file for complete search history.

(56) References Cited

U.S. PATENT DOCUMENTS

| | | |
|---|---|---|
| 5,387,422 A | 2/1995 | Handel et al. |
| 6,413,512 B1 * | 7/2002 | Houston ............ A61K 38/4873 424/94.63 |
| 2003/0095961 A1 | 5/2003 | Houston et al. |

FOREIGN PATENT DOCUMENTS

WO    WO-2014130007 A1 *    8/2014    ............ A23L 33/18

OTHER PUBLICATIONS

"Aspergillopepsin I" Handbook of Proteolytic Enzymes, Third Edition, 2013, Neil D. Rawlings and Guy Salvesen, Academic Press, Chapter 27, p. 135 (Year: 2013).*
International Search Report of PCT/IN2019/050965.
Written Opinion of the International Searching Authority in PCT/IN2019/050965.

* cited by examiner

*Primary Examiner* — Ruth A Davis
(74) *Attorney, Agent, or Firm* — Liang & Hennessey LLP; Stanley Liang (57) ABSTRACT

The present invention provides a novel proteolytic enzyme composition more particularly an orally administered proteolytic enzyme composition comprising of one or more acid proteases, one or more alkaline protease and one or more plant proteases. More particularly, the composition comprises of microbial (fungal, bacterial or other microbes) protease enzymes, proteases from plant and animals proteases thereof.

5 Claims, 5 Drawing Sheets

Figure 1: Effect of different enzyme treatments on degree of protein hydrolysis

Figure 3: BCAAs Bioavailability Enhancement. Comparison of area under the curve (AUC) of BCAAs for Treatment Group A/B and Control Group Figure 4: Total Nitrogen Excretion- Average 24 hour nitrogen excretion between Treatment A/B and Control Group

PROTEOLYTIC ENZYME COMPOSITION

FIELD OF THE INVENTION

The present invention provides a novel proteolytic enzyme composition more particularly an orally administered proteolytic enzyme composition comprising of one or more acid proteases, one or more alkaline protease and one or more plant proteases. More particularly, the composition comprises of microbial (fungal, bacterial or other microbes) protease enzymes, proteases from plant and animals proteases thereof.

BACKGROUND OF THE INVENTION

Proteolytic enzyme, also called protease, proteinase, or peptidase, or a group of enzymes that break the long chain proteins into shorter fragments (peptides) and eventually into their components, the amino acids. Protease enzymes isolated from microbial sources (various strains of fungi, bacteria, etc) have been used as additives in the food processing industry for almost a century (Underkofler, L. A., et al., "Microbiological process report—Production of microbial enzymes and their applications," Applied Microbiology Vol. 6, page 212-221 (1958)). Proteases/enzymes like pepsin, trypsin and pancreatin extracted from animals have been used since decades as an aid for digestion in humans.

Proteolytic enzymes break down dietary protein and protein-based foreign bodies. They function as digestive aids in the gut. It is well established that optimal nutrition and digestion are paramount for improving athletic performance. In addition to health benefits, research suggests that digestive enzyme supplementation may aid athletic performance. To increase the lean muscle mass, athletes rely on various protein supplements to get ample amount of amino acids which are the structural components of muscles. Whey protein is one of the popular protein supplements among athletes and is considered one of the best sources of proteins available.

US 2004/0057944, titled "Microbial Enzyme Mixtures useful to treat digestive disorders" describes mixture of microbial enzymes for the treatment of maldigestion in humans. The enzyme mixture comprises of a concentrated lipase of *Rhizopus delemar*, a neutral protease of *Aspergillus melleus* and an amylase of *Aspergillus oryzae*.

US 20080199448, titled "Enzyme Composition for improving food digestion" discloses a combination of digestive enzymes and L-Glutamine as active ingredients which have therapeutic effects on food absorption and digestion. The combination further comprises of a lipase, an amylase and a protease. The portion of each enzyme is enteric coated.

U.S. Pat. No. 5,387,422, titled "Proteolytic Fungal Enzyme Food Supplement Composition" discloses a proteolytic enzyme food supplement composition wherein the proteolytic enzyme is obtained from fungal source only.

Research suggests that in order to increase or maintain the lean muscle mass, protein intake of 1.5-2.8 g/kg/day is effective for individuals. Protein intake as high as 2.8 g/kg/day (3.5 times the current recommended daily allowance) has been reported to have no adverse effects on renal function. Supplementing the diet with processed whey protein is one of the popular choices to achieve these levels of daily protein consumption. Some products have a suggested per day serving size as high as 50 g of protein. However, due to inability of endogenous digestive enzymes to digest such a large quantity of protein and their rapid transit time in the gastrointestinal tract, approximately only 15 g of the protein is digested and absorbed. The collective effect of these factors may contribute to incomplete digestion, thereby limiting the absorption rate of protein before it reaches the ceacum and is eliminated as waste. It stated that the undigested protein causes issues related to indigestion such as gas bloating, belching and sometimes vomiting and loose motions. Thus, the incomplete digestion reduces the desired positive therapeutic effects, such as increased lean muscle mass, increased $N_2$ retention, and positive cardiovascular effects such as reduced levels of C-reactive protein (CRP). (Anderson, et al., "An open label study to determine the effects of an oral proteolytic enzyme system on whey protein concentrate metabolism in healthy males," Journal of the International Society of Sports Nutrition, 2008, 5:10).

The objective of the present invention, is to develop a novel proteolytic enzyme composition which increases the absorption rate of whey protein in vivo, produces a positive $N_2$ balance and decrease the CRP Levels effectively. As a result of extensive research, the inventors have developed a proteolytic enzyme composition which effectively increases the protein digestibility.

SUMMARY OF THE INVENTION

The present invention relates to a proteolytic enzyme composition. More particularly it relates to a blend of proteolytic enzymes which can be obtained from microbial sources (fungi, bacteria, etc), plant and animals sources and are added to protein supplements.

Accordingly, in a first aspect, the present invention provides a proteolytic enzyme composition comprising of:
a) one or more of an acid protease;
b) one or more of an alkaline protease;
c) one or more of a plant protease.

In an embodiment of the above aspect the proteolytic enzyme composition comprises of:
a) an acid protease;
b) an alkaline protease;
c) a plant protease.

In another embodiment of the above aspect, the proteolytic enzyme composition comprises of:
a) an acid protease;
b) an alkaline protease;
c) two plant proteases.

In one embodiment of the above aspect, the proteolytic enzyme composition comprises of:
a) acid protease enzyme selected from fungal enzyme or bacterial enzyme or a combination of both fungal enzyme and bacterial enzyme.
b) alkaline protease enzyme selected from fungal enzyme or bacterial enzyme or a combination of both fungal enzyme and bacterial enzyme.
c) plant protease enzyme selected from kiwi, papaya, fig, mango and pineapple plants.

In another embodiment of the above aspect, the proteolytic enzyme composition comprises of:
a) acid protease fungal enzyme selected from the group consisting of *Rhizopus oryzae* or *Rhizopus niveus* or *Aspergillus niger* or *Aspergillus oryzae* or the acid protease bacterial enzyme selected from the group consisting of *Bacillus subtilis* or *Bacillus licheniformis*;
b) alkaline protease fungal enzyme selected from the group consisting of *Rhizopus niveus* or *Rhizopus oryzae* or *Aspergillus niger* or *Aspergillus oryzae* or alkaline protease bacterial enzyme is selected from the group consisting of *Bacillus subtilis* or *Bacillus licheniformis*;

c) plant proteases selected from actinidin, papain, ficin and bromelain.

In another embodiment of the above aspect, the acid protease is present in the concentration ranging from about 5% to about 40% w/w; alkaline protease is present in the concentration ranging from about 20% to about 45% w/w; and plant protease enzyme is present in the concentration ranging from about 5% to about 30% w/w of the composition.

In a further embodiment of the above aspect, the concentration of plant proteases actinidin ranges from about 1% to about 10% w/w, the concentration of papain ranges from about 2% to about 15% w/w, the concentration of ficin ranges from about 0.5% to about 5% w/w and the concentration of bromelain ranges from about 7% to about 25% w/w of the composition.

In a yet another embodiment of the above aspect, the weight ratio of acid protease to alkaline protease in the composition ranges from about 1:0.5 to about 1:6. The weight ratio of acid protease to plant protease ranges from about 1:0.1 to about 1:2. The weight ratio of alkaline protease to plant protease ranges from about 1:0.1 to about 1:2. The ratio of actinidin to ficin in the composition ranges from about 1:0.5 to about 1:2 The ratio of papain to bromelain in the composition ranges from about 1:0.5 to about 1:4. Preferably, the weight ratio of acid protease to alkaline protease to plant protease ranges from about 1:0.5: 0.1 to about 1:6:2.

In another embodiment of the above aspect, the proteolytic enzyme composition may additionally comprise a neutral protease, a pancreatin, trypsin, pepsin or a combination thereof. The neutral protease fungal enzyme may be selected from the group consisting of *Rhizopus oryzae* or *Rhizopus niveus* or *Aspergillus niger* or *Aspergillus oryzae* and pancreatin, trypsin and pepsin may be selected from the group consisting of animal pancreas and porcine gastric mucosa. Further, the neutral protease may be present in the concentration ranging from about 5% to about 25% w/w of the composition. The weight ratio of acid protease to neutral protease in the composition ranges from about 1:0.25 to about 1:2. The concentration of pancreatin, trypsin and pepsin (in a combination) ranges from about 1.5% to about 12% w/w of the composition.

In yet another embodiment of the above aspect, there is provided a proteolytic enzyme composition which provides an additional aid to endogenous enzyme system to digest the consumed protein to the maximum extent.

In still another embodiment of the above aspect, the proteolytic enzyme composition works in a broad pH range, ranging from pH 2 to pH 9.

In yet another embodiment of the above aspect, the composition of the present invention increases the digestion and bioavailability of the protein supplement by digesting protein in the wide gastrointestinal pH range of the human digestive system.

In still another embodiment of the above aspect, the proteolytic enzyme composition is administered orally as capsules or as powder with protein supplements.

The aforementioned aspects and embodiments, and other aspects, features and advantages of the present invention will be apparent from the following detailed description.

DETAILED DESCRIPTION OF THE INVENTION

As used herein the following definitions apply unless clearly indicated otherwise. It should also be noted that the singular forms "a" "an" and "the" include plural reference unless the context clearly dictates otherwise.

The proteolytic enzyme composition described herein relates to a blend of proteolytic enzymes which can be obtained from microbial sources (fungi, bacteria, etc) and plant source and are added to protein supplements. The proteolytic enzyme composition comprises one or more acid proteases, one or more alkaline proteases, and one or more plant proteases. All these enzymes are the essential component of the present invention. The proteolytic enzymes from animal origin may be additionally added. Further, the source of acid protease and alkaline protease used, in accordance with the present invention is vital. "Protease enzyme" and "proteolytic enzyme" are used interchangeably herein. All protease enzymes suitable for use in the present invention are commercially available from known sources and can be accessed by a person skilled in the art.

The term "Acid Protease Enzyme" is defined as a protein-digesting enzyme, which exhibits maximum activity and stability in acidic conditions, at pH range of 2.0 to 5.0. Acid proteases have a low isoelectric point and are low in basic amino acids. The acid protease fungal enzymes which can be utilized include those obtained from *Rhizopus oryzae* or *Rhizopus niveus* or *Aspergillus niger* or *Aspergillus oryzae*. The acid protease bacterial enzyme which can be utilized include those obtained from *Bacillus subtilis* or *Bacillus licheniformis*. the acid protease may be present in the concentration ranging from about 5% to about 40% w/w, particularly from about 20% to about 40% w/w of the composition. These enzymes can be obtained commercially and would be known to the person skilled in the art.

The term "Alkaline Protease Enzyme" refers to an endo-protease enzyme capable of hydrolyzing broad range of peptide bonds. The alkaline protease enzymes are active at neutral as well as alkaline pH. The alkaline protease fungal enzymes which can be utilized include those obtained from *Rhizopus niveus* or *Rhizopus oryzae* or *Aspergillus niger* or *Aspergillus oryzae*.

The alkaline protease bacterial enzyme which can be utilized include those obtained from *Bacillus subtilis* or *Bacillus licheniformis*. The alkaline protease may be present in the concentration ranging from about 20% to about 45% w/w of the composition. These enzymes can be obtained either by known methods or can be purchased commercially from the available sources.

The term "plant protease" refers to enzymes selected from the group consisting of actinidin, papain, ficin and bromelain. These enzymes may be obtained from kiwi, papaya, fig and pineapple plants respectively and actinidin is selected from the group consisting of kiwi and mango. The plant protease enzyme may be present in the concentration ranging from about 5% to about 30% w/w of the composition. The concentration of actinidin ranges from about 1% to about 10% w/w, the concentration of papain ranges from about 2% to about 15% w/w, the concentration of ficin ranges from about 0.5% to about 5% w/w and the concentration of bromelain ranges from about 7% to about 25% w/w of the composition. These enzymes can be obtained commercially and would be known to the person skilled in the art.

The term "actinidin" refers to a proteolytic enzyme extracted from either Kiwi fruit or Mango fruit having activity in the pH range of 6-7.

The term "ficin" refers to a proteolytic enzyme extracted from fig having activity in the pH range of 5.5-7.5.

The term "papain" refers to a proteolytic enzyme extracted from papaya plant with pH range of 3-9.

The term "bromelain" refers to a proteolytic enzyme extracted from pineapple juice and stem and is active at pH range of 5-8.

The term "Neutral Protease Enzyme" refers to an endoprotease enzyme capable of hydrolyzing peptide bonds. The neutral protease enzymes are active at neutral pH. The neutral protease fungal enzymes which can be utilized include those obtained from *Rhizopus niveus* or *Rhizopus oryzae* or *Aspergillus niger* or *Aspergillus oryzae*. The neutral protease bacterial enzyme which can be utilized include those obtained from *Bacillus subtilis* or *Bacillus licheniformis*. Further, the neutral protease may be present in the concentration ranging from about 5% to about 25% w/w of the composition. The weight ratio of acid protease to neutral protease in the composition ranges from about 1:0.25 to about 1:2. These enzymes can be obtained either by known methods or can be purchased commercially.

In yet another embodiment of the present invention, the composition is made by combining an effective amount of acid protease enzyme, alkaline protease enzyme, plant proteases, and if desired additional enzymes useful in enhancing the digestive activity of proteins like pepsin, pancreatin and trypsin; and a pharmaceutically acceptable carrier, excipient, adjuvant and/or vehicle. In yet another embodiment, the composition of the present invention besides the preferred enzymes, may include but not limited to additional protease enzymes in the composition which are preferably selected from the group consisting of keratinase, renin, cathepsin, chymotrypsin, subtilisin, thermolysin, endoproteinase, dipase, collagenase and combinations thereof. The concentration of pancreatin, trypsin and pepsin (in a combination) ranges from about 1.5% to about 12% w/w of the composition.

Exemplary excipients include, for example, magnesium stearate, stearic acid, acacia gum, fructose, modified cellulose gum, colloidal silicon dioxide, gelatin, glutens, artificial colours, microcrystalline cellulose, dibasic calcium phosphate, aspartame, and natural flavouring agents.

Carriers may be prepared from a wide range of materials. Without being limited thereto, such materials include diluents, binders and adhesives, lubricants, plasticizers, disintegrants, colorants, bulking substances, flavouring agents, sweeteners and miscellaneous materials such as buffers and adsorbents in order to prepare a particular composition, The proteolytic composition further comprises a carrier material, such as maltodextrin, dextrin, starch, calcium salts, and combinations thereof.

Examples of binding agents suitable for use in the present invention include, but are not limited to croscarmellose sodium, povidone, dextrin, and combinations thereof.

The proteolytic enzyme compositions may preferably be designed to be ingested with protein in order to convert the ingested dietary protein into free amino acids in the gastrointestinal system, which then may be used by the body for muscle synthesis.

Preferably, the composition comprises a solid form such as, for example, a powder, a tablet, a capsule, a caplet, a sachet, or an encapsulated liquid. Particularly preferably, the composition is in the form of a capsule or powder or powder filled in a capsule.

The composition disclosed in U.S. Pat. No. 5,387,422 is a blend of digestive proteases from fungus *Aspergillus niger* and *Aspergillus oryzae* from Triarco Industries. *Aspergillus niger* is an acid protease fungal enzyme and *Aspergillus oryzae* is a semi-alkaline protease fungal enzyme.

The method of component incorporation for the proteolytic enzyme compositions, in accordance with the present invention is described by way of examples. As shown by performing an Application study for degree of protein hydrolysis using enzymes, a combination of acid protease, alkaline protease with plant proteases are very effective in improving the protein digestibility.

In one embodiment, the composition is to be administered orally and added in or taken with protein supplements to improve protein digestion and make it available for muscle building process during anabolic cycles.

According to another embodiment, the compositions works at a broad pH range, ranging from pH 2 to pH 9. The composition is thus active in the digestion window of gastrointestinal tract, wherein protein digestion takes place with a pH as low as pH 2 of the stomach to pH as high as pH 8 of the intestine. The composition is thus constantly active throughout the protein digestive window associated with human digestive system, therefore the amount of amino acid released is increased as compared to the amount generated only by the natural digestive process.

According to yet another embodiment, the composition relates to increasing the digestion and bioavailability of the protein supplement by digesting protein in the wide or broad gastrointestinal pH range of the human digestive system.

EXPERIMENTAL SECTION

All the components were weighed. The enzymes were sieved together and blended for 20 minutes at 15 rpm. Maltodextrin, sodium starch glycolate, microcrystalline cellulose, silicon dioxide, croscarmellose sodium were sieved and blended for 20 minutes at 15 rpm. Both the blends were mixed. Magnesium stearate was sieved and was added to the blend. The formulation was blended for 5 minutes at 15 rpm. The blend was filled in capsules.

The present invention will be further described having reference to the following examples, by way of illustration only.

EXAMPLES

Example 1

| Components | Amount (mg) |
| --- | --- |
| Acid Protease | 56.50 |
| Alkaline Protease | 90.50 |
| Neutral Protease | 14.50 |
| Pancreatin | 7.50 |
| Papain | 17.80 |
| Ficin | 2.00 |
| Trypsin | 12.00 |

-continued

| Components | Amount (mg) |
|---|---|
| Pepsin | 20.00 |
| Maltodextrin | 15.00 |
| Sodium Starch Glycolate | 10.00 |
| Microcrystalline Cellulose | 47.70 |
| Silicon Dioxide | 1.75 |
| Croscarmellose Sodium | 2.75 |
| Magnesium Stearate | 3.00 |
| Total | 300.00 |

Example 2

| Components | Amount (mg) |
|---|---|
| Acid Protease | 78.00 |
| Alkaline Protease | 102.00 |
| Papain | 19.00 |
| Ficin | 6.00 |
| Bromelain | 25.00 |
| Actinidin | 13.00 |
| Microcrystalline Cellulose | 49.00 |
| Silicon Dioxide | 1.00 |
| Croscarmellose Sodium | 4.00 |
| Magnesium Stearate | 3.00 |
| Total | 300.00 |

Example 3

| Components | Amount (mg) |
|---|---|
| Acid Protease | 72.00 |
| Alkaline Protease | 93.00 |
| Actinidin | 14.00 |
| Papain | 12.00 |
| Bromelain | 24.00 |
| Trypsin | 15.00 |
| Maltodextrin | 26.00 |
| Sodium Starch Glycolate | 10.00 |
| Microcrystalline Cellulose | 29.50 |
| Silicon Dioxide | 1.50 |
| Magnesium Stearate | 3.00 |
| Total | 300.00 |

Example 4

| Components | Amount (mg) |
|---|---|
| Acid Protease | 102.00 |
| Alkaline Protease | 70.00 |
| Neutral Protease | 46.20 |
| Papain | 22.00 |
| Pepsin | 5.00 |
| Maltodextrin | 13.00 |
| Microcrystalline Cellulose | 32.50 |
| Silicon Dioxide | 1.80 |
| Croscarmellose Sodium | 4.50 |
| Magnesium Stearate | 3.00 |
| Total | 300.00 |

Example 5

| Component | Amount (mg) |
|---|---|
| Acid Protease | 74.00 |
| Alkaline Protease | 85.00 |
| Neutral Protease | 29.80 |
| Actinidin | 8.20 |
| Bromelain | 28.40 |
| Trypsin | 17.00 |
| Ficin | 6.00 |
| Maltodextrin | 15.60 |
| Microcrystalline Cellulose | 28.50 |
| Silicon Dioxide | 2.80 |
| Croscarmellose Sodium | 1.70 |
| Magnesium Stearate | 3.00 |
| Total | 300.00 |

Example 6

| Component | Amount (mg) |
|---|---|
| Acid Protease | 109.50 |
| Alkaline Protease | 97.00 |
| Papain | 15.00 |
| Bromelain | 28.00 |
| Microcrystalline Cellulose | 48.50 |
| Silicon Dioxide | 2.50 |
| Croscarmellose Sodium | 3.50 |
| Magnesium Stearate | 3.00 |
| Total | 300.00 |

Example 7

| Component | Amount (mg) |
|---|---|
| Acid Protease | 20.00 |
| Alkaline Protease | 108.00 |
| Neutral Protease | 33.00 |
| Pancreatin | 22.00 |
| Papain | 5.00 |
| Actinidin | 10.00 |
| Trypsin | 21.00 |
| Maltodextrin | 19.00 |
| Microcrystalline Cellulose | 54.50 |
| Silicon Dioxide | 1.25 |
| Croscarmellose Sodium | 3.25 |
| Magnesium Stearate | 3.00 |
| Total | 300.00 |

Example 8

| Component | Amount (mg) |
|---|---|
| Acid Protease | 86.50 |
| Alkaline Protease | 97.00 |
| Papain | 23.00 |
| Bromelain | 45.00 |
| Microcrystalline Cellulose | 40.00 |
| Silicon Dioxide | 2.50 |

-continued

| Component | Amount (mg) |
| --- | --- |
| Croscarmellose Sodium | 3.00 |
| Magnesium Stearate | 3.00 |
| Total | 300.00 |

Example 9

| Component | Amount (mg) |
| --- | --- |
| Acid Protease | 72.00 |
| Alkaline Protease | 101.00 |
| Ficin | 15.00 |
| Papain | 15.00 |
| Bromelain | 14.50 |
| Trypsin | 11.00 |
| Maltodextrin | 23.50 |
| Sodium Starch Glycolate | 8.00 |
| Microcrystalline Cellulose | 35.00 |
| Silicon Dioxide | 2.00 |
| Magnesium Stearate | 3.00 |
| Total | 300.00 |

Example 10

| Component | Amount (mg) |
| --- | --- |
| Acid Protease | 92.00 |
| Alkaline Protease | 80.00 |
| Neutral Protease | 35.00 |
| Papain | 35.00 |
| Pepsin | 12.00 |
| Maltodextrin | 15.00 |
| Microcrystalline Cellulose | 23.50 |
| Silicon Dioxide | 1.50 |
| Croscarmellose Sodium | 3.00 |
| Magnesium Stearate | 3.00 |
| Total | 300.00 |

Example 11

The objectives of this study were to hydrolyze whey proteins using proteolytic composition comprising of proteases as herein disclosed to evaluate the degree of hydrolysis (DH) using Ninhydrin method for free alpha-amino nitrogen (FAAN).

Method:
1. About 50 g whey protein mixed with 400 ml water was incubated with enzyme composition at 37° C. for 2 hours
2. Samples at 0, 15, 30, 60, 90, and 120 min were taken and filtered. (Pipette out different volumes (0.1 ml-1 ml) of test/control solution to the respective labelled test tubes.)
3. Added distilled water in all the test tubes to make up the volume to 4 ml.
4. Added 4 ml of distilled water to the test tube labelled blank.
5. Ninhydrin reagent (1 mL) was added to all the test tubes including the test tubes labelled 'blank' and 'unknown'.
6. The contents of the tubes were vortexed.
7. The mouths of the tubes were covered with aluminum foil.
8. The test tubes were placed in boiling water bath for 15 minutes.
9. The test tubes were removed from boiling water, cooled and 1 ml of ethanol was added to each test tube and mixed well.
10. The absorbance was recorded at 570 nm for each solution using a colorimeter.

Experimental Set Up Details:

| Set up Parameters | Value | Unit |
| --- | --- | --- |
| Whey Protein | 50 | g |
| Water Added (RO) | 400 | ml |
| Batch size | 450 | ml |
| Retention time | 120 | minutes |
| Temperature | 37 | ° C. |

TABLE 1

Effect of different enzyme treatments on degree of protein hydrolysis (example 8, example 6, prior art product as per U.S. Pat. No. 5,387,422).

| | FAAN (Free Alfa-Amino Nitrogen) in sample (ppm) | | | | | |
| --- | --- | --- | --- | --- | --- | --- |
| Application Mode | 0 Minute | 15 Minute | 30 Minute | 60 Minute | 90 Minute | 120 Minute |
| Untreated Control | 190 ± 5 | 190 ± 5 | 190 ± 5 | 190 ± 5 | 190 ± 5 | 190 ± 5 |
| Example 6 | 190 ± 5 | 400 ± 5 | 430 ± 5 | 445 ± 5 | 485 ± 5 | 560 ± 5 |
| Example 8 | 190 ± 5 | 415 ± 5 | 420 ± 5 | 435 ± 5 | 475 ± 5 | 500 ± 5 |
| Competitor | 190 ± 5 | 265 ± 5 | 285 ± 5 | 305 ± 5 | 315 ± 5 | 322 ± 5 |

Figure 1:
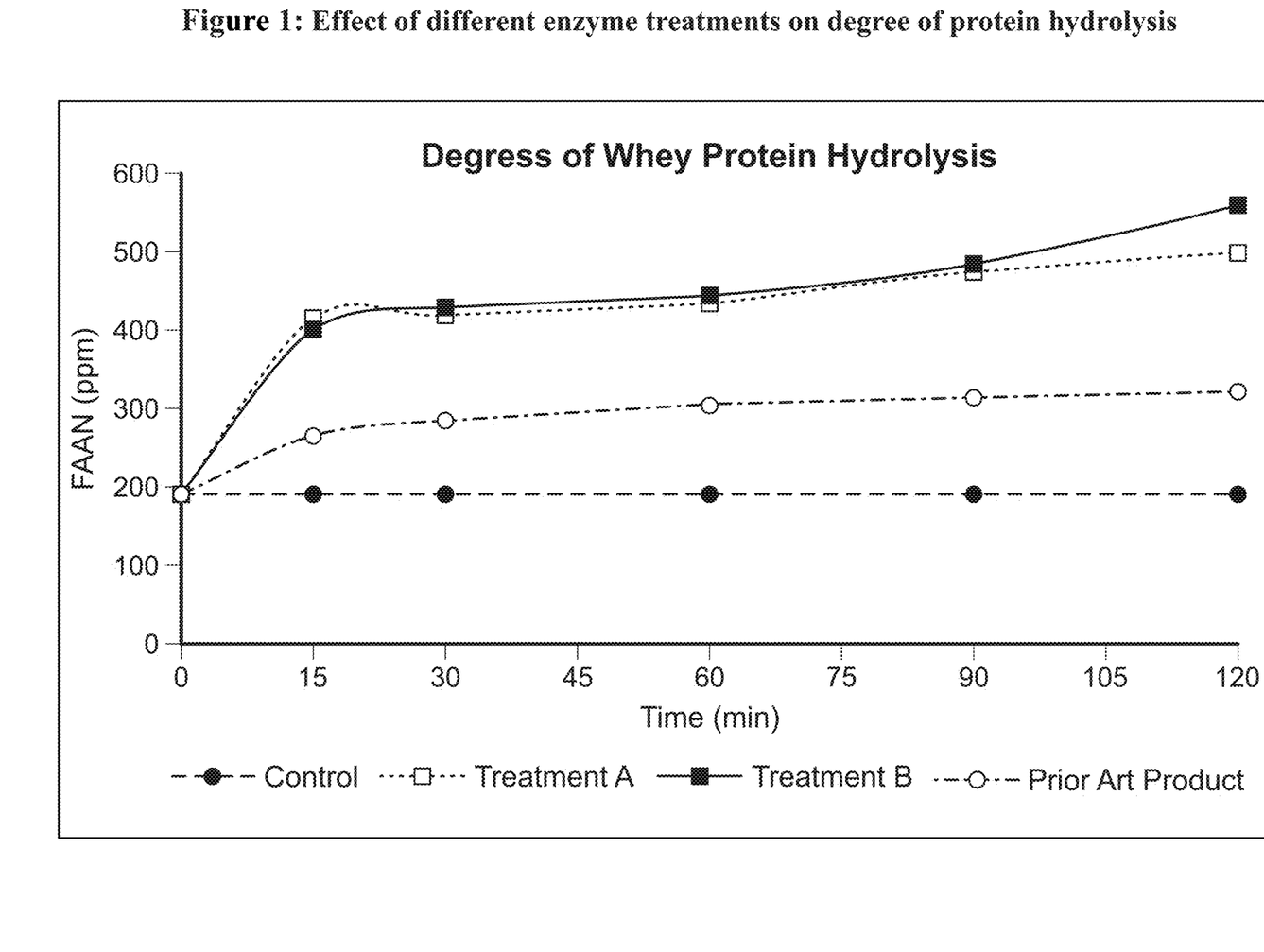
FIG. 1 illustrates the effect of different enzyme treatments on degree of protein hydrolysis.

Based on the observed results, it can be appreciated that Example 6 and Example 8 treated whey protein samples showed higher degree of protein hydrolysis and filtration rate as compared to the prior art product (FIG. 1).

Example 12

A study was performed in 24 healthy, lean, males age 20-36 years, each with a body mass index (BMI) ranging from 20 to 24 under fasting conditions. The study was approved by Independent Ethics Committee (IEC) and was enrolled with the Clinical Trials Registry—India (CTRI/2019/02/017731). Each subject was pre-informed of the purpose, methods, and probable risks associated with the study, and informed consent was signed by each participant.

All the subjects were divided into three equal groups comprising eight subjects in each group. The groups were assigned to either Treatment-A or Treatment-B or Control Group. All subjects received a 50 gram whey protein with 360 mL water either alone (Control Group) or with treatment A (One capsule containing the proteolytic enzyme composition as per Example 8, (commercially available as MB EnzymePro®) or treatment B [Two capsules of MB EnzymePro®] after an overnight fasting of at least 12 hours. All the participants followed a specified, balanced diet of 2200 Kcal/day during the stay at the clinic facility.

The objective of this clinical study was to establish, if MB EnzymePro® (Enhanced Absorption Formula, EAF™) would significantly affect the amount of whey protein metabolized in-vivo and if any effect would be adequate to significantly alter nitrogen ($N_2$) balance and C-reactive protein (CRP) levels as compared to the control group. Comparing levels of total serum amino acids (TSAA) after ingestion, with and without MB EnzymePro®, would be an indicator if the composition of the invention was effective in increasing the amount of digested and absorbed whey protein.

TSAA Levels

Figure 2:
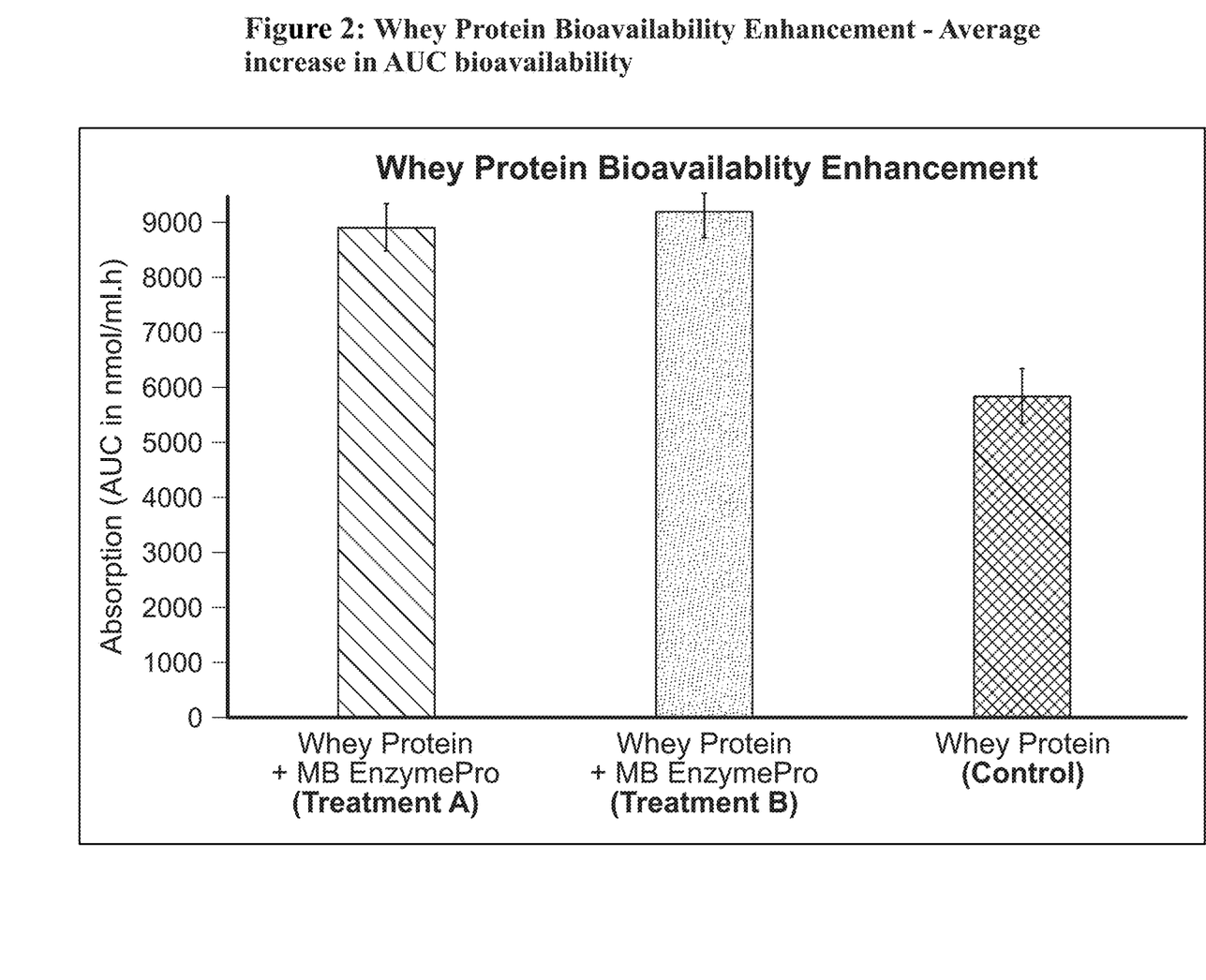
FIG. 2 illustrates Whey Protein Bioavailability Enhancement of IAAs.

Analysis of TSAA kinetic profiles of all treatment groups showed a progressive, time-dependent increase for about 1.5 hours and then a constant decrease till 4 hours. Statistical comparison of means between treatment groups and control group showed differences between groups and all time points to be significant (p=0.05). The results demonstrated that postprandial TSAA levels were significantly increased over control from a 50 gram dose of whey protein co-administered with MB EnzymePro®. This showed that supplementation with MB EnzymePro® in treatment A and B increased the digestion of whey protein leading to increase in its digestion and absorption rate and is additionally supported by significant (1.53 and 1.57 times) increases in the sum of area under the curve (AUC) of individual amino acids (IAAs) (FIG. 2) as compared to the control group. After baseline subtraction, no significant differences were found between the AUC of each treatment A and B representing that the WP absorption rate may be close to maximum in treatment A.

Individual Amino Acid Levels

Figure 3:
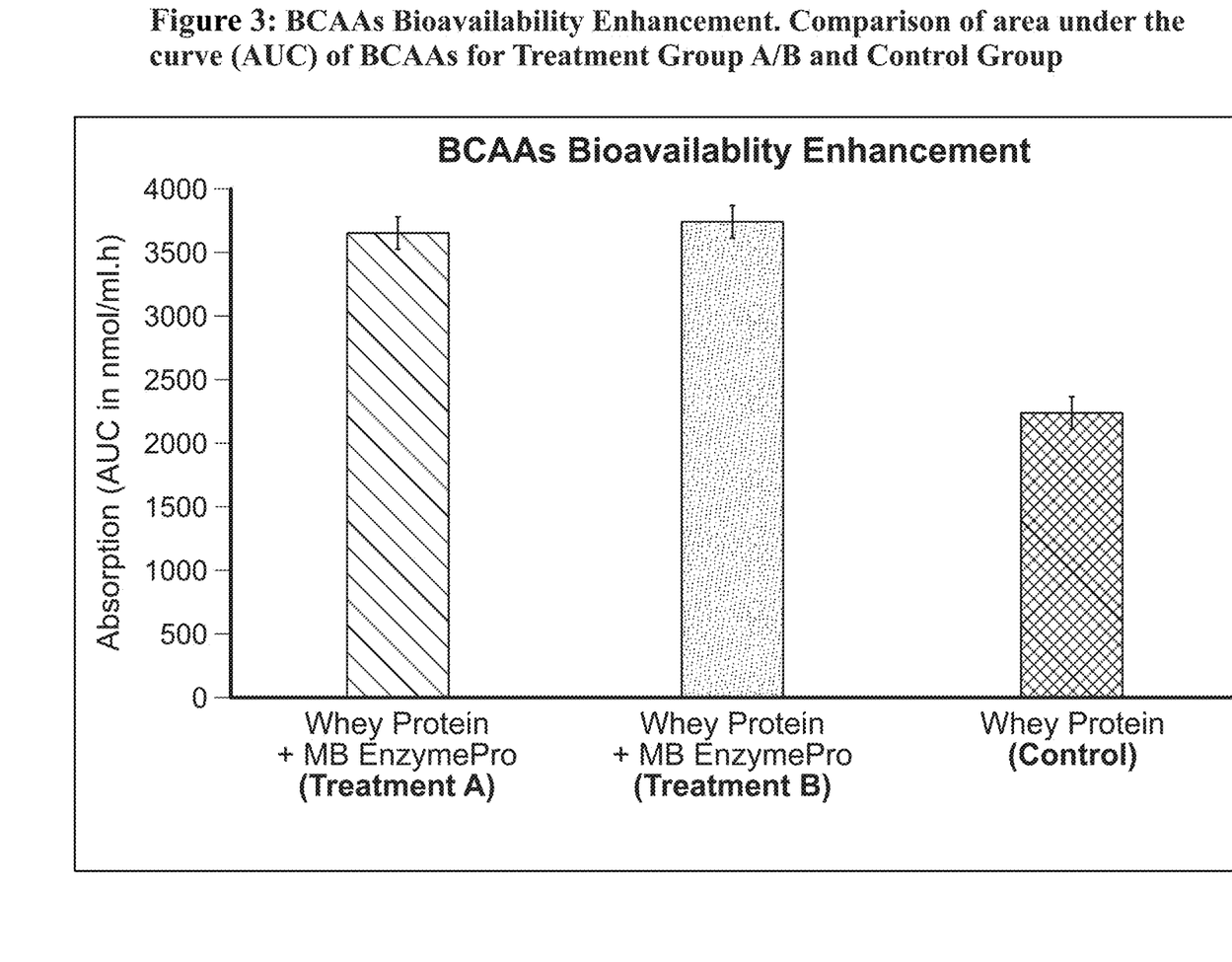
FIG. 3 illustrates Bioavailability Enhancement of BCAAs.

There was an overall increase in individual amino acids (IAA) level for the seventeen amino acids analysed in the treatment groups. There were statistically significant differences between control and treatment groups for cysteine, isoleucine, leucine, lysine, phenylalanine, proline, threonine, tyrosine, methionine and valine (10 of 17). Alanine, glycine, histidine, arginine aspartic acid, glutamic acid, and serine were the amino acids that were not significantly different from the control group. The sum of AUC was significantly greater in each treatment group as compared to the control group (p=0.05). There was a significant increase of 163% and 167% in the AUC of branched amino acids (BCAAs) (sum of AUC of isoleucine, leucine and valine) for treatment group A and B respectively as compared to the control group (FIG. 3).

MB EnzymePro® had a profound increase in the level of amino acids especially the BCAAs. BCAAs are of special importance for bodybuilders and athletes because these amino acids are used by the body to build up the protein for muscle synthesis and muscle repair. BCAAs are essential amino acids that are not produced by the body, therefore, they must be acquired from the diet or from nutritional supplements. BCAAs are metabolized in the muscle rather than in the liver. Consequently, the effect of these BCAAs is much quicker and efficient than that of any other amino acid. If the diet is balanced, BCAAs will be used for protein synthesis, essential for endurance athletes and strenuous workouts. BCAAs are used to reduce fatigue in both anaerobic and endurance sports.

Nitrogen Excretion

Figure 4:
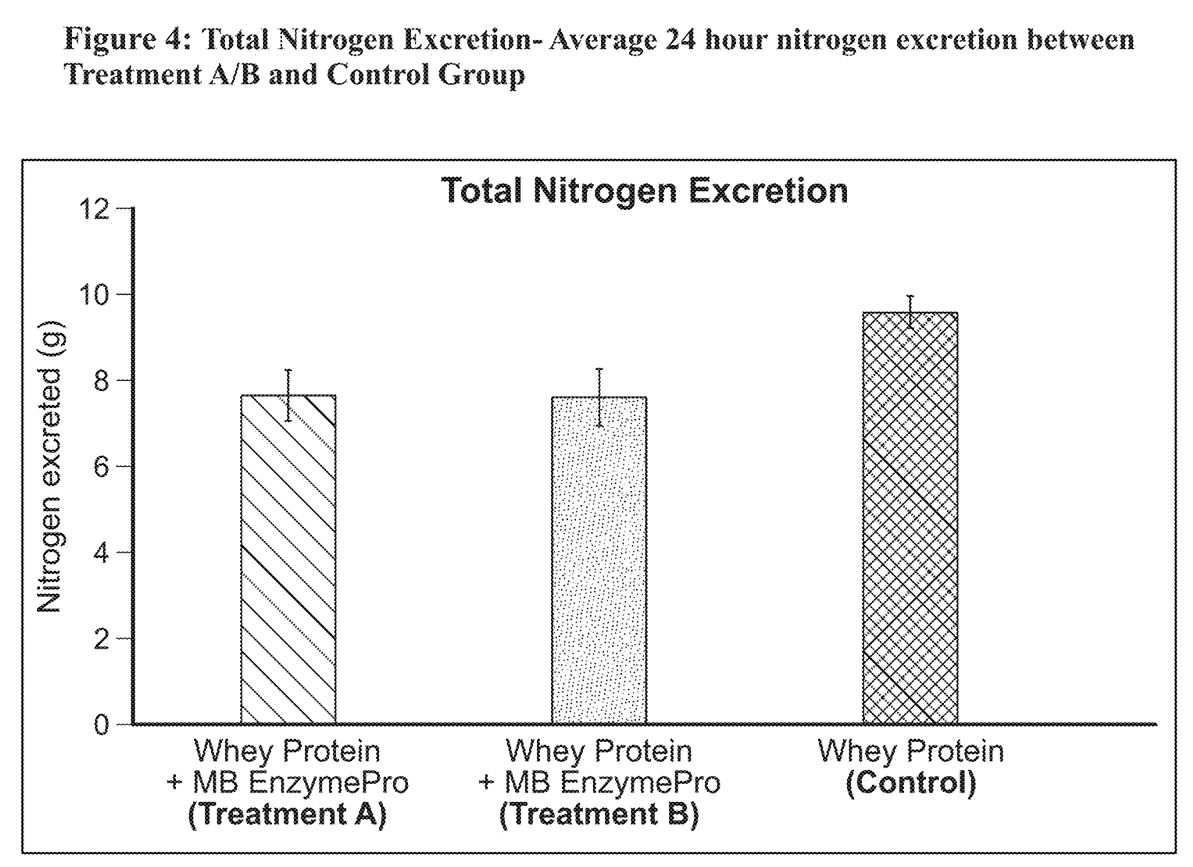
FIG. 4 illustrates Average 24 hour nitrogen excretion between Treatment A/B and Control Group.

The average amount of $N_2$ excreted in 24 hours was determined as urea for both treatment groups and the control group. In the treatment groups A and B, the average amount of $N_2$ excreted over 24 hours was 7.65 g and 7.60 g respectively. In the control group, the average amount of $N_2$ excreted over 24 hours was 9.59 g (FIG. 4). The total nitrogen excretion decreased significantly for both treatment groups A and B with MB EnzymePro®. This array of evidences offers additional support that whole body protein metabolism was decreased in each treatment group. These findings also suggest increased protein utilization.

C-Reactive Protein

Figure 5:
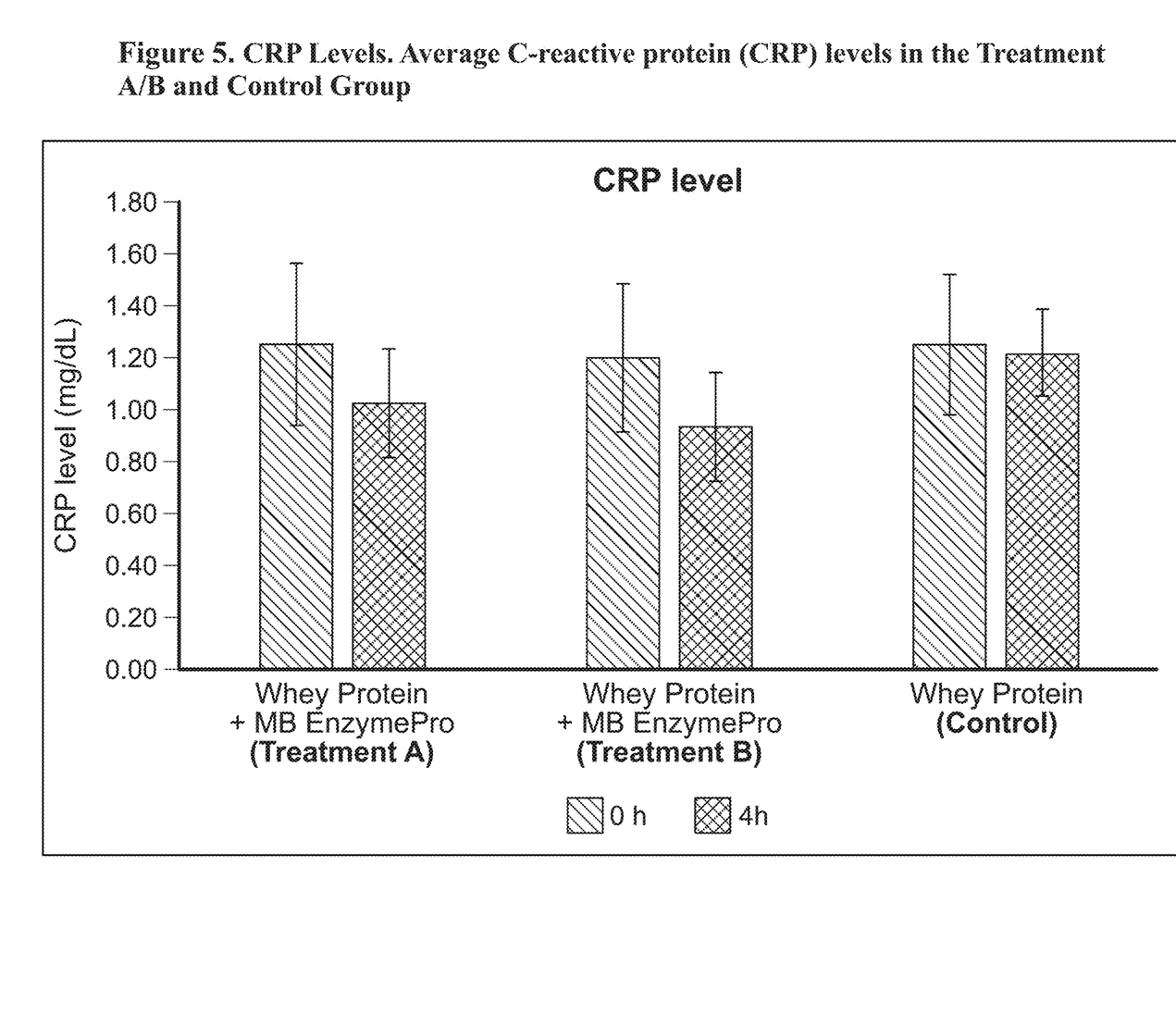
FIG. 5 illustrates Average C-reactive protein (CRP) levels in Control Group and Treatment A/B.

CRP was measured at 0.0 hour and at 4 hours in each treatment group and control group Significant reductions (p=0.003) were found between 0.0 hour and 4 hour in each treatment group as compared to the control group. Treatment group A showed a reduction of 16.15% and treatment group B showed a reduction of 23.61% as compared to the control group at 4 hours (FIG. 5). This may be related to the differences in the amount of whey protein digested and absorbed between the control group and treatment groups. Supplementing whey protein with MB EnzymePro® may contribute to significantly reducing CRP levels by producing bioactive peptides in-vivo.

We claim:

1. A health supplement composition comprising whey protein as protein supplement and proteases comprising an acid protease, an alkaline protease, plant proteases papain and bromelain;
   wherein:
   weight ratio of acid protease to alkaline protease in the composition ranges from about 1:0.5 to about 1:6;
   weight ratio of acid protease to plant proteases ranges from about 1:0.1 to about 1:2;
   weight ratio of alkaline protease to plant proteases ranges from about 1:0.1 to about 1:2; and
   ratio of papain to bromelain in the composition ranges from about 1:0.5 to about 1:4.

2. The health supplement composition of claim 1, wherein:
   a) said acid protease is derived from fungi or bacteria; and
   b) said alkaline protease is derived from fungi or bacteria.

3. The health supplement composition of claim 1, wherein:
   a) said acid protease is derived from of *Rhizopus oryzae, Rhizopus niveus, Aspergillus niger, Aspergillus oryzae, Bacillus subtilis* or *Bacillus licheniformis*; and
   b) said alkaline protease is derived from *Rhizopus oryzae, Rhizopus niveus, Aspergillus niger, Aspergillus oryzae, Bacillus subtilis* or *Bacillus licheniformis*.

4. The health supplement composition of claim 1, further comprising one or more proteases comprising one or more neutral protease, a pancreatin, trypsin, or pepsin.

5. The health supplement composition of claim 1, wherein the composition comprises:

| Component | Amount (mg) |
| --- | --- |
| Acid Protease | 86.50 |
| Alkaline Protease | 97.00 |
| Papain | 23.00 |
| Bromelain | 45.00 |
| Microcrystalline Cellulose | 40.00 |
| Silicon Dioxide | 2.50 |
| Croscarmellose Sodium | 3.00 |
| Magnesium Stearate | 3.00 |
| TOTAL | 300.00. |

* * * * *

UNITED STATES PATENT AND TRADEMARK OFFICE
CERTIFICATE OF CORRECTION

PATENT NO. : 12,220,447 B2
APPLICATION NO. : 17/425582
DATED : February 11, 2025
INVENTOR(S) : Trehan et al.

Page 1 of 1

It is certified that error appears in the above-identified patent and that said Letters Patent is hereby corrected as shown below:

In the Drawings

Line 2, In Figure 1, "Degress of Whey Protein Hydrolysis" should be corrected to "Degrees of Whey Protein Hydrolysis"

Signed and Sealed this
Twenty-fifth Day of March, 2025

Coke Morgan Stewart
*Acting Director of the United States Patent and Trademark Office*